United States Patent [19]

Skuballa et al.

[11] 4,423,067

[45] Dec. 27, 1983

[54] NOVEL CARBACYCLINS, THEIR PREPARATION AND USE

[75] Inventors: Werner Skuballa; Bernd Radüchel; Norbert Schwarz; Helmut Vorbrüggen; Jorge Casals-Stenzel; Ekkehard Schillinger; Michael H. Town, all of Berlin, Fed. Rep. of Germany

[73] Assignee: Schering Aktiengesellschaft, Berlin and Bergkamen, Fed. Rep. of Germany

[21] Appl. No.: 333,099

[22] Filed: Dec. 21, 1981

[30] Foreign Application Priority Data

Dec. 19, 1980 [DE] Fed. Rep. of Germany ....... 3048906

[51] Int. Cl.³ ................. C07C 177/00; A61K 31/557
[52] U.S. Cl. .................................... 424/305; 424/308; 424/317; 424/320; 424/321; 546/342; 548/562; 549/13; 549/79; 549/427; 549/501; 556/437; 560/56; 560/116; 560/119; 560/256; 562/466; 562/498; 562/501; 564/98; 564/158; 564/159
[58] Field of Search ............ 562/466, 501, 498; 560/116, 119, 56, 256; 564/98, 158, 159; 546/342; 549/13, 17, 427, 501; 548/562; 556/437; 424/305, 308, 317, 320, 321, 324

[56] References Cited

FOREIGN PATENT DOCUMENTS

| 2012265 | 7/1979 | United Kingdom ................ 560/119 |
| 2013661 | 8/1979 | United Kingdom ................ 560/119 |
| 2014143 | 8/1979 | United Kingdom ................ 560/119 |

Primary Examiner—Robert Gerstl
Attorney, Agent, or Firm—Millen & White

[57] ABSTRACT

Carbacyclin derivatives of Formula I

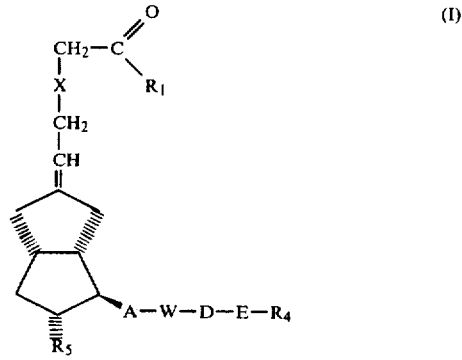

wherein
$R_1$ is $OR_2$, wherein $R_2$ is hydrogen, alkyl, cycloalkyl, aryl, a heterocyclic residue, or $NHR_3$, wherein $R_3$ is an acid residue or hydrogen;
X is oxygen;
A is —$CH_2$—$CH_2$—, trans—CH=CH—, or —C≡C—;
W is free or functionally modified hydroxymethylene or free or functionally modified

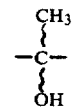

wherein the OH-group can be in the α- or β-position;
D is a straight-chain or branched, saturated or unsaturated aliphatic group of 1-10 carbon atoms, which can optionally be substituted by fluorine atoms, 1,2-methylene, 1,1-trimethylene;
E is —C≡C— or —$CR_6$=$CR_7$— wherein $R_6$ and $R_7$ are hydrogen or alkyl of 1-5 carbon atoms;
$R_4$ is an aliphatic group, cycloalkyl, optionally substituted aryl, or a heterocyclic group;
$R_5$ is free or functionally modified hydroxy and, when $R_2$ is hydrogen, the physiologically compatible salts thereof with bases, have valuable pharmacological properties.

22 Claims, No Drawings

CARBACYCLINS, THEIR PREPARATION AND USE

BACKGROUND OF THE INVENTION

The present invention relates to novel prostacyclin derivatives, a process for their preparation, as well as their use as medicinal agents.

DOS's [German Unexamined Laid-Open Applications] Nos. 2,845,770; 2,900,352; 2,902,442; 2,904,655; 2,909,088; and 2,912,409 disclose (5E)- and (5Z)-6a-carbaprostaglandin-$I_2$ analogs. The nomenclature for the compounds of this invention is based on a proposal by Morton and Brokaw [J. Org. Chem. 44: 2880 (1979)]. In the synthesis of these compounds, two double-bond isomers are produced in all cases, characterized by the notation (5E) or (5Z). The two isomers of this prototype are illustrated by the following structural formulae:

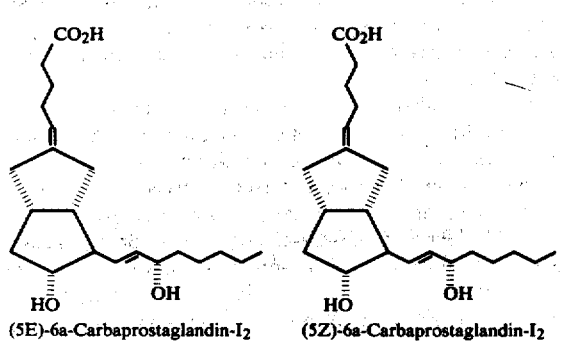

(5E)-6a-Carbaprostaglandin-$I_2$     (5Z)-6a-Carbaprostaglandin-$I_2$

It is known from the very voluminous literature on the state of the art of prostacyclins and their analogs that this class of compounds is suitable for the treatment of mammals, including man because of their biological and pharmacological properties. However, their utilization as medicines frequently encounters difficulties since the duration of their efficacy is too short for therapeutic purposes. All structural alterations are aimed at prolonging the duration of efficacy as well as increasing the selectivity of the effectiveness.

SUMMARY OF THE INVENTION

Accordingly, it is an object of this invention to provide new prostaglandin compounds, i.e., carbacyclins, achieving such ends.

Upon further study of the specification and appended claims, further objects and advantages of this invention will become apparent to those skilled in the art.

It has now been found that, by replacement of the methylene group in the 3-position of the carbacyclin by oxygen, it is possible to attain a longer period of efficacy, higher selectivity, and improved effectiveness. The compounds of this invention have blood-pressure-lowering (concerning vasodilation) and bronchodilatory effects. They are also suitable for inhibition of thrombocyte aggregation and of gastric acid secretion.

Thus, the above objects have been achieved by providing carbacyclin derivatives of Formula I

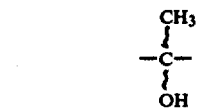

wherein
$R_1$ is $OR_2$, wherein $R_2$ is hydrogen, alkyl, cycloalkyl, aryl, a heterocyclic residue, or $NHR_3$, wherein $R_3$ is an acid residue or hydrogen atom;
X is oxygen;
A is —$CH_2$—$CH_2$—, trans—CH=CH—, or —C≡C—;
W is free or functionally modified hydroxymethylene or free or functionally modified $$\begin{array}{c} CH_3 \\ | \\ -C- \\ | \\ OH \end{array}$$

wherein the OH-group can be in the α- or β-position;
D is a straight-chain or branched, saturated or unsaturated aliphatic group of 1-10 carbon atoms, which can optionally be substituted by fluorine 1,2-methylene or 1,1-trimethylene;
E is —C≡C— or —$CR_6$=$CR_7$— wherein $R_6$ and $R_7$ are different and are hydrogen or alkyl of 1-5 carbon atoms;
$R_4$ is an aliphatic group, cycloalkyl, optionally substituted aryl, or a heterocyclic group;
$R_5$ is free or functionally modified hydroxy; and,
when $R_2$ is hydrogen, the physiologically compatible salts thereof with bases.

DETAILED DISCUSSION

The compounds of Formula I include (5E)- as well as (5Z)-isomers.

Suitable alkyl groups $R_2$ include straight-chain or branched alkyl groups of 1-10 carbon atoms, e.g. methyl, ethyl, propyl, isopropyl, butyl, isobutyl, tert-butyl, pentyl, isopentyl, neopentyl, heptyl, hexyl, decyl, and the like.

The alkyl groups $R_2$ can optionally be mono- to polysubstituted, to form equivalent groups, by halogen atoms (e.g. F, Cl, Br), $C_1$-$C_4$-alkoxy groups, optionally substituted $C_6$-$C_{10}$-aryl groups, di-$C_1$-$C_4$-alkylamines, and tri-$C_1$-$C_4$-alkylammonium. Suitable such substituted aryl groups include those described below as $R_2$ groups per se. Monosubstituted alkyl groups are preferred.

Examples of such substituents include fluorine, chlorine, bromine, phenyl, dimethylamino, diethylamino, methoxy, ethoxy, etc.

Preferred alkyl groups $R_2$ are those of 1-4 carbon atoms, e.g., methyl, ethyl, propyl, dimethylaminopropyl, isobutyl and butyl.

Aryl groups $R_2$ include substituted as well as unsubstituted aryl groups, such as, for example, phenyl, 1-naphthyl, and 2-naphthyl, all of which can respectively be substituted by 1-3 halogen atoms, a phenyl group, 1-3 alkyl groups of 1-4 carbon atoms each, or a chloromethyl, fluoromethyl, trifluoromethyl, carboxy, hydroxy, or alkoxy group of 1-4 carbon atoms. Substitution in the 3- or 4-positions on the phenyl ring is preferred, for example by fluorine, chlorine, alkoxy, or trifluoromethyl, or in the 4-position by hydroxy.

The cycloalkyl group $R_2$ can contain 4-10, preferably 5 or 6 carbon atoms in the ring. The rings can be substituted by alkyl groups of 1-4 carbon atoms. Examples include cyclopentyl, cyclohexyl, methylcyclohexyl, and adamantyl.

Suitable heterocyclic groups $R_2$ include 5- and 6-membered, usually aromatic, heterocycles containing at least one, and preferably one, hetero atom, preferably nitrogen, oxygen, or sulfur. Examples include 2-furyl, 3-furyl, 2-thienyl, 3-thienyl, 2-pyridyl, 3-pyridyl, or 4-pyridyl, etc.

The acid residue $R_3$ includes physiologically compatible acid residues. Preferred acids include organic, usually hydrocarbon, carboxylic acids and sulfonic acids of 1-15 carbon atoms belonging to the aliphatic, cycloaliphatic, aromatic, aromatic-aliphatic, and heterocyclic series. These acids can be saturated, unsaturated and/or polybasic and/or substituted in the usual way. Examples of substituents include $C_1$-$C_4$-alkyl, hydroxy, $C_1$-$C_4$-alkoxy, oxo, or amino groups, or halogen atoms (F, Cl, Br). All of these acids are essential equivalents, e.g., the heterocyclic acids are equivalent for these purposes to the hydrocarbon acids.

The following carboxylic acids are cited as examples: formic acid, acetic acid, propionic acid, butyric acid, isobutyric acids, valeric acid, isovaleric acid, caproic acid, enanthic acid, caprylic acid, pelargonic acid, capric acid, undecylic acid, lauric acid, tridecyclic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di-, and trichloroacetic acids, aminoacetic acid, diethylaminoacetic acid, piperidinoacetic acid, diethylaminoacetic acid, piperidinoacetic acid, morpholinoacetic acid, lactic acid, succinic acid, adipic acid, benzoic acid, benzoic acids substituted by halogen or trifluoromethyl, hydroxy, alkoxy, or carboxy groups, nicotinic acid, isonicotinic acid, furan-2-carboxylic acid, cyclopentylpropionic acid, etc.

Examples of sulfonic acids include methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino-, N-methylpiperazino-, and morpholinosulfonic acids.

Especially preferred acyl residues are those of up to 10 carbon atoms.

The hydroxy groups $R_5$ and those in W can be functionally modified, e.g. by etherifying or esterifying, wherein the free or modified hydroxy groups in W can be in the α- or β-position. Free hydroxy groups are preferred.

Suitable ether and acyl residues are familiar to persons skilled in the art. Ether residues which can be readily split off are preferred, for example, tetrahydropyranyl, tetrahydrofuranyl, α-ethoxyethyl, trimethylsilyl, dimethyl-tert-butylsilyl, or tri-p-benzylsilyl residues. Suitable acyl residues include those described for $R_3$; specific examples include acetyl, propionyl, butyryl, benzoyl, etc. Many other equivalents of such residues exist and are well known.

The groups $R_4$ include straight chain or branched, aliphatic groups which are saturated or unsaturated, preferably saturated ones, of 1-10, especially 1-7 carbon atoms, which can optionally be substituted by aryl, which latter can optionally be substituted as described for $R_2$ above. Examples include alkyl and alkenyl, such as methyl, ethyl, propyl, butyl, isobutyl, tert-butyl, pentyl, hexyl, heptyl, octyl, butenyl, isobutenyl, propenyl, pentenyl, hexenyl, benzyl, and p-chlorobenzyl.

The cycloalkyl group $R_4$ can contain 4-10 ring atoms, preferably 5 or 6 carbon atoms. The rings can be substituted by alkyl groups of 1-4 carbon atoms. Examples include cyclopentyl, cyclohexyl, methylcyclohexyl, and adamantyl.

Suitable substituted or unsubstituted aryl groups $R_4$ include, for example: phenyl, 1-naphthyl, and 2-naphthyl, each of which can be substituted by 1-3 halogen atoms, a phenyl group, 1-3 alkyl groups of 1-4 carbon atoms each, or a chloromethyl, fluoromethyl, trifluoromethyl, carboxy, $C_1$-$C_4$-alkoxy, or hydroxy group. Substitution in the 3- and 4-positions on the phenyl ring is preferred, for example, by fluorine, chlorine, $C_1$-$C_4$-alkoxy, or trifluoromethyl, or in the 4-position by hydroxy.

Suitable heterocyclic groups $R_4$ include 5- and 6-membered, usually aromatic, heterocycles, containing at least one, and preferably one, hetero atom, preferably nitrogen, oxygen, or sulfur. Examples include: 2-furyl, 2-thienyl, 2-pyridyl, 3-pyridyl, 4-pyridyl, 3-furyl, 3-thienyl, and others.

Suitable alkylene groups D include straight-chain or branched, saturated and unsaturated alkylene-type aliphatic residues, preferably saturated ones of 1-10, especially 1-5 carbon atoms, which can optionally be substituted by fluorine atoms, 1,2-methylene or, 1,1-trimethylene. Examples include methylene, fluoromethylene, ethylene, 1,2-propylene, ethylethylene, trimethylene, tetramethylene, pentamethylene, 1-methyltetramethylene, 1-methyltrimethylene, 1,1-trimethyleneethylene etc. Especially preferred compounds of this invention are those with E as $-C\equiv C-$ or $-CR_6=CR_7-$, wherein $R_6$ and $R_7$ are both alkyl of 1-5 carbon atoms.

For salt formation with the free acids ($R_1$=H), suitable are inorganic and organic bases. These are familiar to those skilled in the art for the formation of physiologically compatible salts. Examples include alkali metal hydroxides, such as sodium and potassium hydroxide, alkaline earth metal hydroxides, e.g. calcium hydroxide, ammonia, amines, such as ethanolamine, diethanolamine, triethanolamine, N-methylglucamine, morpholine, tris(hydroxymethyl)-methylamine, etc.

The present invention furthermore relates to a process for the preparation of the prostane derivatives of this invention, comprising, in a conventional manner, etherifying a compound of Formula II

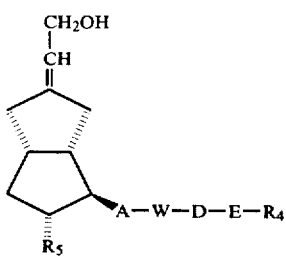

(II)

wherein R4, R5, A, W, D, and E are as defined above, in the presence of a base, optionally after blockage of any free hydroxy groups present, with a haloacetic acid derivative of Formula III

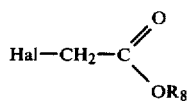

(III)

wherein

Hal represents a chlorine or bromine atom and $R_8$ is an alkyl residue or an alkali metal, and thereafter, optionally, in any chosen sequence, separating isomers and/or liberating blocked hydroxy groups and/or esterifying a free carboxy group and/or saponifying an esterified carboxy group or converting a carboxy group into an amide or, with a physiologically compatible base, into a salt.

The reaction of the compound of Formula II with a haloacetic acid derivative of Formula III is conducted at temperatures of 0° C. to 100° C., preferably 10°–80° C., in an aprotic solvent or solvent mixture, e.g. dimethyl sulfoxide, dimethylformamide, tetrahydrofuran, etc. Suitable bases are those known to person skilled in the art for etherifications, for example sodium hydride, potassium tert-butylate, butyllithium, etc.

The saponification of the prostaglandin esters is carried out according to methods known to those skilled in the art, for example using basic catalysts.

The ester group $-OR_2$ for $R_1$, wherein $R_2$ is an alkyl group of 1–10 carbon atoms or cycloalkyl or heterocyclic, is introduced by methods known to those skilled in the art. The carboxy compounds can be reacted, for example, with diazo hydrocarbons in a conventional way. The esterification with diazo hydrocarbons can be effected, for example, by mixing a solution of the diazo hydrocarbon in an inert solvent, preferably in diethyl ether, with the carboxy compound in the same or in another inert solvent, e.g. methylene chloride. After the reaction is completed in 1–30 minutes, the solvent is removed and the ester purified in the usual way. Diazoalkanes are either known or can be prepared by the following conventional methods [Org. Reactions 8: 389–394 (1954)].

The introduction of the ester group $-OR_2$ for $R_1$ wherein $R_2$ is a substituted or unsubstituted aryl group or aromatic heterocyclics, also takes place according to methods known to those skilled in the art. For example, the carboxy compounds can be reacted with the corresponding arylhydroxy compounds using cyclohexylcarbodiimide in the presence of a suitable base, e.g. pyridine or triethylamine, in an inert solvent. Suitable solvents include methylene chloride, ethylene chloride, chloroform, ethyl acetate, tetrahydrofuran, preferably chloroform. The reaction is carried out at temperatures between −30° C. and +50° C., preferably at +10° C.

The prostaglandin derivatives of general Formula I wherein $R_1$ is a hydroxy group can be converted into salts with suitable amounts of the corresponding inorganic bases under neutralization procedures. For example, when the corresponding PG acids are dissolved in water containing the stoichiometric quantity of the base, the solid inorganic salt is obtained after evaporation of the water or after adding a water-miscible solvent, e.g. alcohol or acetone.

The amine salts are produced as usual. For this purpose, the PG acid is dissolved, for example, in a suitable solvent such as ethanol, acetone, diethyl ether, or benzene, and at least the stoichiometric amount of the amine is added to this solution. The salt is thus usually obtained in the solid form or is isolated in the usual way after evaporation of the solvent.

The functional modification of the free OH-groups also can be performed according to methods known to persons skilled in the art. For example, to introduce the ether blocking groups, the reaction can be carried out with dihydropyran in methylene chloride or chloroform with the use of an acidic condensation agent, e.g. p-toluenesulfonic acid. The dihydropyran is used in excess, preferably in four to 10 times the amount of the theoretical need. The reaction is normally completed at 0° C. to 30° C. after 15–30 minutes.

The acyl blocking groups are introduced by conventionally reacting a compound of general Formula I with a carboxylic acid derivative, e.g. an acid chloride, an acid anhydride, and others.

The liberation of a functionally modified OH—group to obtain the compounds of Formula I also takes place according to known methods. For example, ether blocking groups can be split off in an aqueous solution of an organic acid, e.g. acetic acid, propionic acid, etc., or in an aqueous solution of an inorganic acid, e.g. hydrochloric acid. To improve solubility, a water-miscible, inert organic solvent is suitably added. Organic solvents that can be used include, for example, alcohols, e.g. methanol and ethanol, and ethers, such as dimethoxyethane, dioxane, and tetrahydrofuran. Tetrahydrofuran is preferably employed. The splitting-off is carried out preferably at temperatures of 20° C. to 80° C.

Silyl ether blocking groups can be split off, for example, with tetrabutylammonium fluoride. Examples of suitable solvents include tetrahydrofuran, diethyl ether, dioxane, methylene chloride, etc. The splitting-off step is preferably conducted at temperatures of 0° C. to 80° C.

The acyl groups can be saponified, for example, with alkali metal or alkaline earth metal carbonates or hydroxides in an alcohol or in the aqueous solution of an alcohol. Suitable alcohols include aliphatic alcohols, e.g. methanol, ethanol, butanol, etc., preferably methanol. Alkali metal carbonates and hydroxides include potassium and sodium salts, but the potassium salts are preferred. Suitable alkaline earth metal carbonates and hydroxides include, for example, calcium carbonate, calcium hydroxide, and barium carbonate. The reaction takes place at −10° C. to 70° C., preferably at 25° C.

The amide group $NHR_3$ for $R_1$ can be introduced by methods known to those skilled in the art. The carboxylic acids of Formula I ($R_2$=H) are first converted with chloroformic acid isobutyl ester into the mixed anhydride in the presence of a tertiary amine, e.g. triethylamine. The reaction of the mixed anhydride with the alkali metal salt of the corresponding amide or with ammonia ($R_3$=H) can be performed in an inert solvent or solvent mixture, e.g. tetrahydrofuran, dimethoxyethane, dimethylformamide, hexamethylphosphoric triamide, at temperatures of $-30°$ to $+60°$ C., preferably at $0°$ to $30°$ C.

Another alternative for introducing the amide group $NHR_3$ for $R_1$ residues is reacting a 1-carboxylic acid of Formula I ($R_2$=H) wherein free hydroxy groups are optionally blocked intermediarily, with compounds of Formula IV

O=C=N—$R_3$  IV wherein $R_3$ is as defined above.

The reaction of a compound of Formula I ($R_1$=OH) with an isocyanate of Formula IV is optionally conducted with the addition of a tertiary amine, e.g. triethylamine or pyridine. The reaction can be accomplished without a solvent or in an inert solvent, preferably acetonitrile, tetrahydrofuran, acetone, dimethylacetamide, methylene chloride, diethyl ether, toluene, etc. at temperatures of $-80°$ to $100°$ C., preferably at $0°$ to $30°$ C.

If the starting compound contains OH-groups in the prostane residue, these OH-groups also react. If, in the end, products are desired which contain free hydroxy groups in the prostane residue, starting compounds are suitablly employed wherein these free hydroxy groups are intermediarily blocked by ether or acyl residues which preferably can be easily split off.

The compounds of Formula II serving as the starting material can be prepared, for example, by reacting, in an olefin-forming reaction in a conventional procedure, an aldehyde of Formula V (DOS No. 2,845,770, which is incorporated by reference herein)

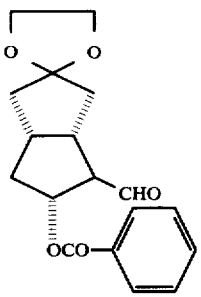
V with a phosphonate of Formula VI

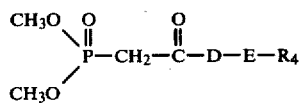
VI wherein D, E, and $R_4$ are as defined above, to obtain a ketone of Formula VII

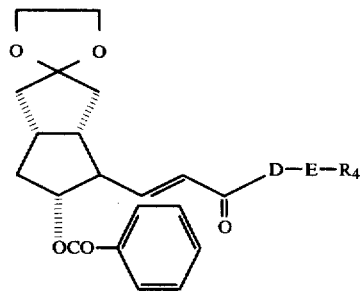
VII

After reduction of the keto group with zinc borohydride or sodium borohydride, or reaction with alkyl magnesium bromide or alkyl lithium and subsequent separation of epimers as well as optional hydrogenation of the double bond, the compounds of Formula VIII are obtained:

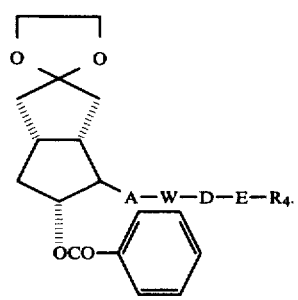
VIII

Saponification of the ester group, for example with potassium carbonate in methanol and splitting of the ketal with aqueous acetic acid as well as optional functional modification of the free hydroxy groups, for example by etherification with dihydropyran, yields the ketone of Formula IX:

$$\underset{R_5}{\text{IX}}$$

After olefin-forming reaction with the triethyl ester of phosphonoacetic acid or the trimethyl ester of phosphonoacetic acid, and subsequent reduction with lithium aluminum hydride, the compounds of Formula II, isomeric on the double bond, are obtained. These can optionally be separated.

The phosphonates of Formula VI can be prepared in a manner known per se by reacting the anion of the dimethyl ester of methylphosphonic acid with a conventional ester of Formula X:

$$\underset{R_6O}{\overset{O}{\diagdown}}C-D-E-R_4 \quad X$$

wherein

D, E, R$_4$ are as defined above and

R$_6$ is an alkyl group of 1-5 carbon atoms.

The compounds of this invention have blood-pressure-lowering and bronchodilatory effects. They are also suitable for inhibition of thrombocyte aggregation. Consequently, the novel prostacyclin derivatives of Formula I represent valuable pharmaceutically active agents. Moreover, as compared to corresponding prostaglandins, they exhibit, with a similar spectrum of activity, a higher specificity and, above all, an essentially longer efficacy. As compared with PGI$_2$, they are distinguished by higher stability. The high tissue specificity of the novel prostaglandis can be demonstrated in an investigation on smooth-muscle organs, such as, for example, on the guinea pig ileum or on the isolated rabbit trachea, where a substantially lower stimulation can be observed than in the administration of natural prostaglandins of the E-, A-, or F-type.

The novel prostaglandin analogs possess the properties typical for prostacyclins, such as, for example lowering of the peripheral arterial and coronary vascular resistance, inhibition of thrombocyte aggregation, and dissolution of platelet thrombi, myocardial cytoprotection, and consequently lowering of systemic blood pressure without simultaneously lowering the stroke volume and coronary blood flow; treatment for strokes, prophylaxis and therapy of coronary heart disease, coronary thrombosis, cardiac infarction, peripheral arterial diseases, arteriosclerosis, and thrombosis, prophylaxis and therapy of ischaemic attacks of the CNS-system, therapy of shock, inhibition of bronchoconstriction, inhibition of gastric acid secretion and cytoprotection of the gastric and intestinal mucosas; cytoprotection in the liver and pancreas, antiallergic properties, lowering of pulmonary vascular resistance and pulmonary blood pressure, promotion of kidney blood flow, utilization in place of heparin or as adjuvant in dialysis of hemofiltration, preservation of blood plasma stores, especially blood platelet preserves, inhibition of labor, treatment of gestational toxicosis, enhancement of cerebral blood flow, etc. In addition, the novel prostaglandin analogs exhibit antiproliferative properties. The prostacyclins of the invention can also be used in combination, for example with β-blockers or diuretics.

The dosage of the compounds generally is 1-1500 μg/kg/day when administered to human patients. The unit dosage for the pharmaceutically acceptable vehicles usually is 0.01-100 mg.

Upon intravenous injection administered to nonanesthetized, hypertonic rats in doses of 5, 20, and 100 μg/kg body weight, the compounds of this invention exhibit a stronger blood-pressure-lowering effect and a more prolonged duration of efficacy than PGE$_2$ and PGA$_2$ without triggering diarrhea, as does PGE$_2$, or cardiac arrhythmias, as does PGA$_2$.

Upon intravenous injection administered to narcotized rabbits, the compounds of this invention show, as compared with PGE$_2$ and PGA$_2$, a stronger and also considerably prolonged blood-pressure-lowering effect without affecting other smooth-muscle organs or organ functions.

For parenteral administration, sterile, injectable, aqueous or oily solutions can be utilized. Suitable for oral administration are, for example, tablets, dragees, or capsules.

The present invention, accordingly, also relates to medicinal agents based on the compounds of Formula I and conventional excipients and vehicles and to their use as described above, for example, as blood-pressure-lowering agents.

In general, the administration of the compounds of this invention is analogous to that of the known agents Prostacyclin (PGI$_2$) and Ciloprost (INN of a new carbacyclin derivate described in U.S. Ser. No. 086,506 filed Oct. 19, 1979).

Each of the novel prostaglandin analogs of this invention is surprisingly and unexpectedly more useful than one of the corresponding conventional prostaglandings or prostacyclins described above for at least one of the pharmacological purposes indicated above, because it has a different and narrower spectrum of biological potency than the known prostaglandins, and therefore is more specific in its activity and causes smaller and fewer undesired side effects than when the prostaglandin is used for the same purpose. Moreover, because of its prolonged activity, fewer and smaller doses of the novel prostaglandin analogs are frequently effective in attaining the desired result.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In all examples which follow, both (5Z) and (5E) isomers were prepared.

EXAMPLE 1

(5E)-(16RS)-16-Methyl-3-oxa-18,18,19,19-tetradehydro-6a-carbaprostaglandin-I$_2$ At 10° C., 0.77 ml of a 1.52-molar butyllithium solution in hexane is added to a solution of 530 mg of 2-{(E)-(1S,5S,6R,7R)-7-(tetrahydropyran-2-yloxy)-6-[(E)-(3S,4RS)-4-methyl-3-(tetrahydropyran-2-yloxy)oct-1-en-6-ynyl]bicyclo[3,3,0]-octan-3-ylidene}ethan-1-ol in 3 ml of tetrahydrofuran; the mixture is agitated for 5 minutes, combined with 3 ml of dimethyl formamide and 4 ml of dimethyl sulfoxide, and then 225 mg of chloroacetic acid lithium salt is added thereto. The mixture is stirred for 24 hours at room temperature, poured on ice water, acidified with 10% citric acid solution, extracted with ether, the organic extract washed once with brine, dried over magnesium sulfate, and evaporated under vacuum. After chromatography of the residue on silica gel, 290 mg of (5E)-(16RS)-16-methyl-3-oxa-18,18,19,19-tetradehydro-6a-carbaprostaglandin-I$_2$ 11,15-bis(tetrahydropyranyl ether) is obtained with ethyl acetate/isopropanol (8+2). To split off the blocking groups, 290 mg of the bis(tetrahydropyranyl ether) is stirred with 28 ml of a mixture of acetic acid/water/tetrahydrofuran (65+35+10) for 16 hours at room temperature and then evaporated under vacuum. The residue is chromatographed with ethyl acetate/acetic acid (99+1) on silica gel. Yield: 105 mg of the title compound as a colorless oil.

The starting material for the above title compound is produced as follows:

1a: 2-{(E)-(1S,5S,6R,7R)-7-(Tetrahydropyran-2-yloxy)-6-[(E)-(3S,4RS)-4-methyl-3-(tetrahydropyran-2-yloxy)-oct-1-en-6-ynyl]bicyclo[3,3,0]octan-3-ylidene}ethan-1-ol At 0° C., 1.73 g of potassium tert.-butylate is added to a solution of 4.0 g of the triethyl ester of phosphonoacetic acid in 80 ml of tetrahydrofuran; the mixture is agitated for 10 minutes, combined with a solution of 4.45 g of (1R,5S,6R,7R)-7-(tetrahydropyran-2-yloxy)-6-[(E)-(3S,4RS)-4-methyl-3-(tetrahydropyran-2-yloxy)oct-1-en-6-ynyl]bicyclo[3,3,0]octan-3-one in 45 ml of toluene, and stirred for 20 hours at room temperature. The mixture is diluted with 600 ml of ether, shaken once with water, once with 20% sodium hydroxide solution, washed neutral with water, dried over magnesium sulfate, and evaporated under vacuum. The residue is filtered with hexane/ether (3+2) over silica gel, thus obtaining 3.7 g of the unsaturated ester as a colorless oil.

IR: 2945, 2870, 1700, 1655, 970 cm$^{-1}$.

1.2 g of lithium aluminum hydride is added in incremental portions at 0° C. to a stirred solution of 3.9 g of the ester as produced above in 130 ml of ether, and the mixture is agitated for 30 minutes at 0° C. The excess reagent is destroyed by the dropwise addition of ethyl acetate, 6 ml of water is added, and the mixture is stirred for 2 hours at 20° C., filtered, and evaporated under vacuum. The residue is chromatographed with ether/hexane (3+2) on silica gel, thus producing, as the less polar compound, 1.05 g of 2-{(Z)-(1S,5S,6R,7R)-7-(tetrahydropyran-2-yloxy)-6-[(E)-(3S,4RS)-4-methyl-3-(tetrahydropyran-2-yloxy)oct-1-en-6-ynyl]bicyclo-[3,3,0]octan-3-ylidene}ethan-1-ol and 2.2 g of the title compound as colorless oils.

IR: 3605, 3450, 2940, 2865, 1600, 970 cm$^{-1}$.

EXAMPLE 2

(5Z)-(16RS)-16-Methyl-3-oxa-18,18,19,19-tetradehydro-6a-carbaprostaglandin-I$_2$ Analogously to Example 1, 490 mg of the Z-configured allyl alcohol prepared according to Example 1a yields 85 mg of the title compound as a colorless oil.

IR (CHCl$_3$): 3340 (broad), 2920, 1722, 1600, 1420, 966 cm$^{-1}$.

EXAMPLE 3

(5E)-(16RS)-16,20-Dimethyl-3-oxa-18,18,19,19-tetradehydro-6a-carbaprostaglandin-I$_2$ In analogy to Example 1, 0.5 g of 2-{(E)-(1S,5S,6R,7R)-7-(tetrahydropyran-2-yloxy)-6-[(E)-(3S,4RS)-4-methyl-3-(tetrahydropyran-2-yloxy)non-1-en-6-ynyl]-bicyclo[3,3,0]octan-3-ylidene}ethan-1-ol and 220 mg of chloroacetic acid lithium salt yield 260 mg of (5E)-(16RS)-16,20-dimethyl-3-oxa-18,18,19,19-tetradehydro-6a-carbaprostaglandin-I$_2$ 11,15-bis(tetrahydropyranyl ether). After the blocking groups have been split off, 90 mg of the title compound is obtained as a colorless oil.

IR: 3400 (broad), 2920, 1721, 1600, 1420, 966 cm$^{-1}$.

The starting material for the above title compound is produced as follows:

3a: (1R,5S,6R,7R)-3,3-Ethylenedioxy-7-benzoyloxy-6-[(E)-(3S,4RS)-3-hydroxy-4-methyl-non-1-en-6-ynyl]-bicyclo[3,3,0]octane At 0° C., a solution of 9.02 g of the dimethyl ester of 3-methyl-2-oxo-oct-5-ynylphosphonic acid in 67 ml of dimethoxy ethane (DME) is added dropwise to a suspension of 1.46 g of sodium hydride (55% suspension in oil) in 130 ml of DME, and the mixture is stirred for 1 hour at 0° C. Thereafter the mixture is combined at −20° C. with a solution of 9.4 g of (1R,5S,6R,7R)-3,3-ethylenedioxy-7-benzoyloxy-6-formylbicyclo[3,3,0]octane in 130 ml of DME, agitated for 1.5 hours at −20° C., poured on 600 ml of saturated ammonium chloride solution, and extracted three times with ether. The organic extract is washed neutral with water, dried over magnesium sulfate, and evaporated under vacuum. Chromatography of the residue on silica gel yields with ether/hexane (1+1) 9.1 g of the α,β-unsaturated ketone as an oil.

At −40° C., 5.2 g of sodium borohydride is added in incremental portions to a solution of 9.1 g of the ketone in 300 ml of methanol, and the mixture is agitated for 1 hour at −40° C. Then the mixture is diluted with ether, washed neutral with water, dried over magnesium sulfate, and evaporated under vacuum. Column chromatography on silica gel with ether/hexane (7+3) yields initially 3.9 g of the title compound (PG nomenlature: 15α-hydroxy) and also, as the more polar component, 3.2 g of the isomeric 15β-hydroxy compound.

IR: 3600, 3400 (broad), 2942, 1711, 1603, 1588, 1276, 968, 947 cm$^{-1}$.

3b: (1R,5S,6R,7R)-7-(Tetrahydropyran-2-yloxy)-6-[(E)-(3S,4RS)-3-(tetrahydropyran-2-yloxy)-4-methyl-non-1-en-6-ynyl]bicyclo[3,3,0]octan-3-one A mixture of 3.6 g of the α-alcohol prepared according to Example 3a and 1.4 g of potassium carbonate in 120 ml of methanol is stirred for 16 hours at room temperature under argon. The mixture is then evaporated under vacuum, diluted with ether, and washed neutral with brine. The product is dried over magnesium sulfate and evaporated under vacuum. The residue from the evaporation is stirred for 16 hours at room temperature with 75 ml of a mixture of acetic acid/water/tetrahydrofuran (65+35+10) and then evaporated under vacuum. Filtration of the residue over silica gel yields, with ethyl acetate/hexane (7+3), 2.2 g of the ketone as an oil.

A solution of 2.2 g of the ketone, 2.4 ml of dihydropyran, and 23 mg of p-toluenesulfonic acid in 75 ml of methylene chloride is stirred for 30 minutes at 0° C. The mixture is then diluted with ether, shaken with dilute sodium bicarbonate solution, washed with water to render the mixture neutral, dried over magnesium sulfate, and evaporated under vacuum.

Yield: 3.4 g of the bis(tetrahydropyranyl ether) which is used without purification.

IR: 2960, 2865, 1738, 970 cm$^{-1}$.

3c: 2-{(E)-(1S,5S,6R,7R)-7-(Tetrahydropyran-2-yloxy)-6-[(E)-(3S,4RS)-4-methyl-3-(tetrahydropyran-2-yloxy)-non-1-en-6-ynyl]bicyclo[3,3,0]octan-3-ylidene}ethan-1-ol In analogy to Example 1a, 3.3 g of the ketone prepared according to Example 3b yields, after separation of isomers by chromatography, as the less polar compound 720 mg of 2-{(Z)-(1S,5S,6R,7R)-7-(tetrahydropyran-2-yloxy)-6-[(E)-(3S,4RS)-4-methyl-3-(tetrahydropyran-2-yloxy)non-1-en-6-ynyl]-bicyclo[3,3,0]octan-3-ylidene}ethan-1-ol and 1.6 g of the title compound as colorless oil.

IR: 3600, 3430, 2942, 2863, 1600, 972 cm$^{-1}$.

EXAMPLE 4

(5Z)-(16RS)-16,20-Dimethyl-3-oxa-18,18,19,19-tetradehydro-6a-carbaprostaglandin-I$_2$ Analogously to Example 1, 0.65 g of the Z-configured allyl alcohol prepared according to Example 3c yields 120 mg of the title compound as a colorless oil.

IR: 3320 (broad), 2925, 1720, 1600, 1420, 968 cm$^{-1}$.

EXAMPLE 5

(5E)-(16RS)-16,20-Dimethyl-3-oxa-19,19,20,20-tetradehydro-6a-carbaprostaglandin-$I_2$ In analogy to Example 1, 0.75 g of 2-{(E)-(1S,5S,6R,7R)7-(tetrahydropyran-2-yloxy)-6-[(E)-(3S,4RS)-4-methyl-3-(tetrahydropyran-2-yloxy)non-1-en-7-ynyl]-bicyclo[3,3,0]octan-3-ylidene}ethan-1-ol and 330 mg of chloroacetic acid lithium salt yield 420 mg of (5E)-(16RS)-16,20-dimethyl-3-oxa-19,19,20,20-tetradehydro-6a-carbaprostaglandin-$I_2$ 11,15-bis-(tetrahydropyranyl ether). After the blocking groups have been split off, 180 mg of the title compound is obtained as a colorless oil.

IR: 3410 (broad), 2925, 1722, 1601, 1420, 965 cm$^{-1}$.

The starting material for the above title compound is prepared as follows:

5a: 3-Methyl-2-oxo-oct-6-ynylphosphonic Acid Dimethyl Ester 109 g of p-toluenesulfonic acid chloride is added to a solution of 40 g of 3-pentyn-1-ol in 240 ml of pyridine, and the mixture is stirred for 48 hours at 0° C. Subsequently 30 ml of water is added, the mixture is stirred for 2 hours and diluted with ether. The mixture is then shaken in succession with 5% sulfuric acid, with water, with 5% sodium bicarbonate solution, washed neutral with water, dried over magnesium sulfate, and evaporated under vacuum. The residue is recrystallized from hexane/ether, thus obtaining 80 g of the tosylate (mp 43° C.).

34 g of methylmalonic ester is added to a suspension of 8.7 g of sodium hydride (55% suspension in oil) and the mixture is refluxed for 4 hours. Subsequently 35 g of 1-tosyloxy-3-pentyne and 130 ml of DME are added at room temperature, and the mixture is heated for 8 hours under reflux, then neutralized with acetic acid, combined with 130 ml of water, extracted with ether, shaken three times with water, dried over magnesium sulfate, and evaporated under vacuum. The residue is purified by vacuum distillation at 12 torr [mm Hg]. At 150°-156° C., 24 g of the alkylated methylmalonic acid ester is obtained which is heated under reflux in 160 ml of dimethyl sulfoxide and 1.5 ml of water for 6 hours with 7.5 g of lithium chloride. The mixture is then poured on 400 ml of ice water, extracted with ether, the organic extract shaken twice with water, dried over magnesium sulfate, and concentrated under vacuum. Distillation of the residue yields at 92° C. and 12 torr 14 g of the ethyl ester of 2-methylhept-5-ynoic acid as a colorless fluid.

At −70° C., 73 ml of a 1.7-molar butyllithium solution in hexane is added dropwise to a solution of 18.6 g of the dimethyl ester of methanephosphonic acid in 280 ml of tetrahydrofuran; the mixture is stirred for 15 minutes and a solution of 10.5 g of 2-methylhept-5-ynoic acid ethyl ester in 48 ml of tetrahydrofuran is gradually added thereto. The mixture is stirred for 4 hours at −70° C., neutralized with acetic acid, and evaporated under vacuum. The distillation of the residue under vacuum at 0.6 torr and 130° C. yields 10.8 g of the title compound as a colorless fluid.

5b: (1R,5S,6R,7R)-3,3-Ethylenedioxy-7-benzoyloxy-6-[(E)-(3S,4RS)-3-hydroxy-4-methylnon-1-en-7-ynyl]-bicyclo[3,3,0]octane Analogously to Example 3a, 12.2 g of (1R,5S,6R,7R)-3,3-ethylenedioxy-7-benzoyloxy-6-formylbicyclo[3,3,-0]octane and 11.9 g of the phosphonate prepared according to Example 5a result in 14.5 g of the unsaturated ketone which, by reduction with 8.2 g of sodium borohydride, is converted into 5.3 g of the title compound.

IR: 3600, 3410, 2940, 1712, 1602, 1588, 1277, 970, 948 cm$^{-1}$.

5c: (1R,5S,6R,7R)-7-(Tetrahydropyran-2-yloxy)-6-[(E)-(3S,4RS)-3-(tetrahydropyran-2-yloxy)-4-methyl-non-1-en-7-ynyl]bicyclo[3,3,0]octan-3-one In analogy to Example 3b, 5.3 g of the α-alcohol prepared according to Example 5b yields 5.4 g of the bis(tetrahydropyranyl ether) as a colorless oil.

IR: 2963, 2866, 1737, 968 cm$^{-1}$.

5d: 2-{(E)-(1S,5S,6R,7R)-7-Tetrahydropyran-2-yloxy)-6-[(E)-(3S,4RS)-4-methyl-3-(tetrahydropyran-2-yloxy)-non-1-en-7-ynyl]bicyclo[3,3,0]octan-3-ylidene}-ethan-1-ol Analogously to Example 1a, 5.3 g of the ketone produced as described in Example 5c yields, after separating the isomers by chromatography, as the less polar compound 1.4 g of 2-{(Z)-(1S,5S,6R,7R)-7-(tetrahydropyran-2-yloxy)-6-[(E)-(3S,4RS)-4-methyl-3-(tetrahydropyran-2-yloxy)non-1-en-7-ynyl]-bicyclo[3,3,0]octan-3-ylidene}ethan-1-ol and 2.9 g of the title compound as a colorless oil.

IR: 3610, 3400, 2940, 2862, 1600, 970 cm$^{-1}$.

EXAMPLE 6

(5Z)-(16RS)-16,20-Dimethyl-3-oxa-19,19,20,20-tetradehydro-6a-carbaprostaglandin-$I_2$ In analogy to Example 1, 810 mg of the Z-configured allyl alcohol prepared according to Example 5d yields 180 mg of the title compound as a colorless oil.

IR: 3430 (broad), 2030, 1721, 1600, 1425, 968 cm$^{-1}$.

EXAMPLE 7

(5E)-(15RS)-15-Methyl-3-oxa-18,18,19,19-tetradehydro-6a-carbaprostaglandin-$I_2$ In analogy to Example 1, 0.45 g of 2-{(E)-(1S,5S,6R,7R)-7-(tetrahydropyran-2-yloxy)-6-[(E)-(3RS)-3-methyl-3-(tetrahydropyran-2-yloxy)oct-1-en-6-ynyl]bicyclo[3,3,0]octan-3-ylidene}ethan-1-ol and 210 mg of chloroacetic acid lithium salt yield 270 mg of (5E)-(15RS)-15-methyl-3-oxa-18,18,19,19-tetradehydro-6a-carbaprostaglandin-$I_2$ 11,15-bis(tetrahydropyranyl ether). After splitting off the blocking groups, 108 mg of the title compound is obtained as a colorless oil.

IR: 3410 (broad), 2945, 1729, 1600, 968 cm$^{-1}$.

The starting material for the above title compound is produced as follows:

7a: 2-{(E)-(1S,5S,6R,7R)-7-(Tetrahydropyran-2-yloxy)-6-[(E)-(3RS)-3-methyl-3-(tetrahydropyran-2-yloxy)-oct-1-en-6-ynyl]bicyclo[3,3,0]octan-3-ylidene}-ethan-1-ol In analogy to Example 1a, 1.7 g of (1R,5S,6R,7R)-7-(tetrahydropyran-2-yloxy)-6-[(E)-(3RS)-3-methyl-3-(tetrahydropyran-2-yloxy)oct-1-en-6-ynyl]bicyclo[3,3,0]octan-3-one yields, after separating the isomers by chromatography, as the less polar compound 320 mg of 2-{[(Z)-(1S,5S,6R,7R)-7-tetrahydropyran-2-yloxy)oct-1-en-6-ynyl]bicyclo[3,3,0]octan-3-ylidene}ethan-1-ol, and 950 mg of the title compound as a colorless oil.

IR: 3600, 3400, 2945, 2865, 1600, 970 cm$^{-1}$.

EXAMPLE 8

(5E)-3-Oxa-18,18,19,19-tetrahydro-6a-carbaprostaglandin-$I_2$

Analogously to Example 1, 0.92 g of 2-{(E)-(1S,5S,6R,7R)-7-(tetrahydropyran-2-yloxy)-6-[(E)-3-(tetrahydropyran-2-yloxy)oct-1-en-6-ynyl]bicyclo[3,3,0]octan-3-ylidene}ethan-1-ol and 430 mg of chloroacetic acid lithium salt yield 510 mg of (5E)-3-oxa-18,18,19,19-tetradehydro-6a-carbaprostaglandin-$I_2$ 11,15-bis(tetrahydropyranyl ether). After subsequent splitting off of the blocking groups, 245 mg of the title compound is obtained as a colorless oil.

IR: 3400 (broad), 2225, 1722, 1600, 972 cm$^{-1}$.

The starting material for the above title compound is prepared as follows:

8a: 2-{(E)-(1S,5S,6R,7R)-7-(Tetrahydropyran-2-yloxy)-6-[(E)-3-(tetrahydropyran-2-yloxy)oct-1-en-6-ynyl]-bicyclo[3,3,0]octan-3-ylidene}ethan-1-ol Analogously to Example 1a, 3.35 g of (1R,5S,6R,7R)-7-(tetrahydropyran-2-yloxy)-6-[(E)-3-tetrahydropyran-2-yloxy)-oct-1-en-6-ynyl]bicyclo[3,3,-0]octan-3-one yields, after separating the isomers by chromatography, as the less polar compound 820 mg of 2-{(Z)-(1S,5S,6R,7R)-7-(tetrahydropyran-2-yloxy)-6-[(E)-3-(tetrahydropyran-2-yloxy)oct-1-en-6-ynyl]bicyclo[3,3,0]-octan-3-ylidene}ethan-1-ol and 1.9 g of the title compound as a colorless oil.

IR: 3600, 3405, 2943, 2865, 1600, 968 cm$^{-1}$.

EXAMPLE 9

(5E)-(16RS)-16,19-Dimethyl-3-oxa-18,19-didehydro-6a-carbaprostaglandin-$I_2$ Analogously to Example 1, 0.97 g of 2-{(E)-(1S,5S,6R,7R)-7-(tetrahydropyran-2-yloxy)-6-[(1E)-(3S,4RS)-4,7-dimethyl-3-(tetrahydropyran-2-yloxy)octa-1,6-dienyl]-bicyclo[3,3,0]octan-3-ylidene}ethan 1-ol and 450 mg of chloroacetic acid lithium salt yield 490 mg of (5E)-(16RS)-16,19-dimethyl-3-oxa-18,19-didehydro-6a-carbaprostaglandin-$I_2$ 11,15-bis(tetrahydropyranyl ether). The subsequent step of splitting off the blocking groups results in 160 mg of the title compound as an oil.

IR: 3410 (broad), 2925, 1720, 1600, 965 cm$^{-1}$.

The starting material for the above title compound is prepared as follows:

9a: (1R,5S,6R,7R)-3,3-Ethylenedioxy-7-benzoylocy-6-[(1E)-(3S,4RS)-3-hydroxy-4,7-dimethylocta-1,6-dienyl]-bicyclo[3,3,0]octane In analogy to Example 3a, 6.5 g of (1R,5S,6R,7)-3,3-ethylenedioxy-7-benzoyloxy-6-formylbicyclo[3,3,0]octane and 6 g of the dimethyl ester of 2-oxo-3,6-dimethylhept-5-enylphosphonic acid yield 6.3 g of the unsaturated ketone which is converted, by reduction with 4 g of sodium borohydride, into 2.7 g of the title compound.

IR: 3600, 3420, 2945, 1713, 1602, 1587, 1278, 972, 948 cm$^{-1}$.

9b: (1R,5S,6R,7R)-7 -(Tetrahydropyran-2-yloxy)-6-[(1E)-(3S,4RS)-4,7-dimethyl-3-(tetrahydropyran-2-yloxy)octa-1,6-dienyl]bicyclo[3,3,0]octan-3-one Analogously to Example 3b, 2.7 g of the α-alcohol produced according to Example 9a yields 2.6 g of the title compound as a colorless oil.

IR: 2965, 2865, 1738, 965 cm$^{-1}$.

9c 2-{(E)-(1S,5S,6R,7R)-7-(Tetrahydropyran-2-yloxy)-6-[(1E)-(3S,4RS)-4,7-dimethyl-3-(tetrahydropyran-2-yloxy)octa-1,6-dienyl]bicyclo[3,3,0]octan-3-ylidene}ethan-1-ol Analogously to Example 1a, 2.6 g of the ketone prepared as described in Example 9b yields, after chromatographic separation of isomers, as the less polar compound 0.65 g of 2-{(Z)-(1S,5S,6R,7R)-7-(tetrahydropyran-2-yloxy)-6-[(1E)-(3S,4RS)-4,7-dimethyl-3-tetrahydropyran-2-yloxy)-octa-1,6-dienyl]bicyclo[3,3,-0]octan-3-ylidene}ethan-1-ol and 1.4 g of the title compound as a colorless oil.

IR: 3600, 3400 (broad), 2945, 2860, 1600, 968 cm$^{-1}$.

EXAMPLE 10

(5E)-(16RS)-16-Methyl-3-oxa-18,18,19,19-tetradehydro-6a-carbaprostaglandin-$I_2$ Methyl Ester A solution of 150 mg of the acid prepared according to Example 1 is combined, in 10 ml of methylene chloride at 0° C., dropwise with an ethereal diazomethane solution until a permanent yellow coloring is produced. After evaporation of the solution under vacuum, the residue is filtered with methylene chloride/isopropanol (95+5) over silica gel, thus obtaining 120 mg of the methyl ester as a colorless oil.

IR: 3600, 3400, 2960, 1740, 1600, 972 cm$^{-1}$.

EXAMPLE 11

(5E)-(16RS)-16-Methyl-3-oxa-18,18,19,19-tetradehydro-N-methanesulfonyl-6a-carbaprostaglandin-$I_2$ Carboxamide At 0° C., a solution of 360 mg of the acid prepared as described in Example 1 in 8 ml of dimethylformamide is combined with 160 mg of the isobutyl ester of chloroformic acid and 120 mg of triethylamine. After 30 minutes, 480 mg of the sodium salt of methylsulfonamide (produced from methylsulfonamide and sodium methylate) and 2 ml of hexamethylphosphoric triamide are added and the mixture stirred for 3 hours at 20° C. Thereafter the reaction mixture is poured on citrate buffer (pH 5), extracted repeatedly with ethyl acetate, and the organic phase is washed with brine, dried over magnesium sulfate, and evaporated under vacuum. Chromatography of the residue on silica gel with methylene chloride/isopropanol yields 160 mg of the title compound as an oil.

IR: 3600, 3400 (broad), 1730, 1600, 970 cm$^{-1}$.

EXAMPLE 12

(5E)-(16RS)-16-Methyl-3-oxa-18,18,19,19-tetradehydro-6a-carbaprostaglandin-$I_2$ Acetylamide At 25° C., 130 mg of triethylamine is added to a solution of 500 mg of (5E)-(16RS)-16-methyl-3-oxa-18,18,19,19-tetradehydro-6a-carbaprostaglandin-$I_2$ 11,15-bis(tetrahydropyranyl ether) in 15 ml of acetonitrile; the mixture is cooled to 0° C., and a solution of 95 mg of acetylisocyanate in 10 ml of acetonitrile is added dropwise thereto. The reaction mixture is agitated for 2 hours at 25° C., concentrated under vacuum, diluted with 100 ml of water, adjusted to pH 5 by adding 1 N hydrochloric acid, extracted with ether, the organic phase washed with brine, dried over magnesium sulfate, and evaporated under vacuum. To split off the blocking groups, the residue is stirred with 15 ml of glacial acetic acid/water/tetrahydrofuran (65/25/10) overnight at 30° C. and evaporated to dryness under vacuum. The residue is chromatographed on silica gel with methylene chloride/1% isopropyl alcohol, thus producing 205 mg of the title compound as an oil.

IR: 3600, 3400, 1708, 976 cm$^{-1}$.

EXAMPLE 13

(5E)-(16RS)-16-Methyl-3-oxa-18,18,19,19-tetradehydro-6a-carbaprostaglandin-I$_2$ Carboxamide 200 mg of (5E)-(16RS)-methyl-3-oxa-18,18,19,19-tetradehydro-6a-carbaprostaglandin-I$_2$ is dissolved in 5 ml of tetrahydrofuran and combined at 0° C. with 80 mg of triethylamine and 90 mg of the isobutyl ester of chloroformic acid. After 1 hour, ammonia in gaseous form is introduced at 0° C. for 10 minutes whereupon the mixture is left at 25° C. for 1 hour. Then the mixture is diluted with 50 ml of water, extracted three times with respectively 30 ml of methylene chloride, the combined extracts are shaken with 20 ml of brine, dried over magnesium sulfate, and evaporated under vacuum. The product is purified by chromatography on silica gel with chloroform/ethyl acetate (8+2), thus obtaining 150 mg of the title compound as an oil.

IR: 3600, 3540, 3410, 2960, 1670, 978 cm$^{-1}$.

EXAMPLE 14

(5E)-(16RS)-16-Methyl-3-oxa-18,18,19,19-tetradehydro-6a-carbaprostaglandin-I$_2$ Tris(hydroxymethyl)aminomethane Salt At 65° C., a solution of 60 mg of tris(hydroxymethyl)aminomethane in 0.2 ml of water is added to a solution of 200 mg of (5E)-(16RS)-16-methyl-3-oxa-18,18,19,19-tetradehydro-6a-carbaprostaglandin-I$_2$ in 35 ml of acetonitrile. The mixture is allowed to cool under stirring, decanted from the solvent after 16 hours, and the residue dried under vacuum. In this way, 190 mg of the title compound is isolated as a viscous oil.

EXAMPLE 15

Composition of an ampoule:

0.5 mg (5E)-(16RS)-16-Methyl-3-oxa-18,18,19,19-tetradehydro-6a-carbaprostaglandin-I$_2$
8.9 mg NaCl
1.212 mg Tromethamol
0.01 ml Ethanol (96%)
and will be brought with 0,01 n HCl-solution to pH 8,3 ad 1 ml with water for injection purposes.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A carbacyclin derivative of the formula:

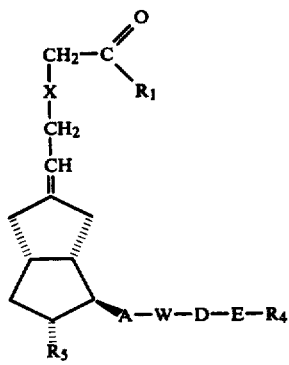

wherein
R$_1$ is OR$_2$ or NHR$_3$,
R$_2$ is hydrogen; C$_{1-10}$ alkyl; C$_{1-10}$ alkyl substituted by halogen, C$_{1-4}$ alkoxy, C$_{6-10}$ aryl, C$_{6-10}$ aryl substituted as defined below for R$_2$ aryl, di-C$_{1-4}$-alkylamino or tri-C$_{1-4}$-alkylammonium; C$_{4-10}$-cycloalkyl; C$_{4-10}$-cycloalkyl substituted by C$_{1-4}$-alkyl; C$_{6-10}$-aryl; C$_{6-10}$-aryl substituted by 1-3 halogen atoms, a phenyl group, 1-3 alkyl groups of 1-4 carbon atoms each, or a chloromethyl, fluoromethyl, trifluoromethyl, carboxy, hydroxy, or alkoxy group of 1-4 carbon atoms; or a 5- or 6-membered aromatic heterocycle containing one O, N or S atom, all other atoms being C- atoms;
R$_3$ is hydrogen or an acyl group of a C$_{1-15}$ hydrocarbon carboxylic or sulfonic acid;
X is oxygen;
A is a —CH$_2$—CH$_2$—, trans—CH=CH—, or —C≡C—group;
W is a free or functionally modified hydroxymethylene group or a free or functionally modified

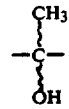

group wherein the OH-group can be in the α- or β-position;
R$_5$ is a free or functionally modified hydroxy group;
wherein the term "functionally modified" refers to replacement of the H-atom on the hydroxy group with an acyl group of a C$_{1-15}$ hydrocarbon carboxylic or sulfonic acid or tetrahydropyranyl, tetrahydrofuranyl, p-ethoxyethyl, trimethylsilyl, dimethyl-tert-butylsilyl, or tri-p-benzylsilyl;
D is C$_{1-10}$ alkylene, or C$_{2-10}$ alkenylene, each optionally substituted by fluorine, 1,2-methylene or 1,1-trimethylene;
E is —C≡C—;
R$_4$ is a C$_{1-10}$ aliphatic group; a C$_{1-10}$ aliphatic group substituted by C$_{6-10}$-aryl or C$_{6-10}$-aryl in turn substituted as defined for R$_2$ above; C$_{4-10}$-cycloalkyl; C$_{4-10}$-cycloalkyl substituted by C$_{1-4}$ alkyl; C$_{6-10}$-aryl; C$_{6-10}$-aryl substituted as defined for R$_2$ aryl above; or a 5- or 6-membered aromatic heterocycle containing one O, N or S-atom, all other atoms being C-atoms; or, when R$_2$ is hydrogen, a physiologically compatible salt thereof with a base.

2. (5E)-(16RS)-16-Methyl-3-oxa-18,18,19,19-tetradehydro-6a-carbaprostaglandin-$I_2$, a compound of claim 1.

3. (5Z)-(16RS)-16-Methyl-3-oxa-18,18,19,19-tetradehydro-6a-carbaprostaglandin-$I_2$, a compound of claim 1.

4. (5E)-(16RS)-16-20-Dimethyl-3-oxa-18,18,19,19-tetradehydro-6a-carbaprostaglandin-$I_2$, a compound of claim 1.

5. (5Z)-(16RS)-16,20-Dimethyl-3-oxa-18,18,19,19-tetradehydro-6a-carbaprostaglandin-$I_2$, a compound of claim 1.

6. (5E)-(16RS)-16,20-Dimethyl-3-oxa-19,19,20,20-tetradehydro-6a-carbaprostaglandin-$I_2$, a compound of claim 1.

7. (5Z)-(16RS)-16,20-Dimethyl-3-oxa-19,19,20,20-tetradehydro-6a-carbaprostaglandin-$I_2$, a compound of claim 1.

8. (5E)-(15RS)-15-Methyl-3-oxa-18,18,19,19-tetradehydro-6a-carbaprostaglandin-$I_2$, a compound of claim 1.

9. (5E)-3-Oxa-18,18,19,19-tetradehydro-6a-carbaprostaglandin-$I_2$, a compound of claim 1.

10. (5E)-(16RS)-16-Methyl-3-oxa-18,18,19,19-tetradehydro-6a-carbaprostaglandin-$I_2$ methyl ester, a compound of claim 1.

11. (5E)-(16RS)-16-Methyl-3-oxa-18,18,19,19-tetradehydro-N-methanesulfonyl-6a-carbaprostaglandin-$I_2$ carboxamide, a compound of claim 1.

12. (5E)-(16RS)-16-Methyl-3-oxa-18,18,19,19-tetradehydro-6a-carbaprostaglandin-$I_2$ acetylamide, a compound of claim 1.

13. (5E)-(16RS)-16-Methyl-3-oxa-18,18,19,19-tetradehydro-6a-carbaprostaglandin-$I_2$ carboxamide, a compound of claim 1.

14. (5E)-(16RS)-16-Methyl-3-oxa-18,18,19,19-tetradehydro-6a-carbaprostaglandin-$I_2$ tris(hydroxymethyl)aminomethane salt, a compound of claim 1.

15. A compound of claim 1 wherein $R_1$ is OH

16. A compound of claim 1 wherein $R_5$ is OH; W is hydroxymethylene or

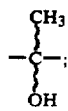

$R_1$ is OH; and $R_4$ is alkyl.

17. A compound of claim 1 wherein $R_5$ is OH; W is hydroxymethylene or

$R_1$ is OH; and $R_4$ is alkyl.

18. A compound of claim 1 wherein $R_5$ is OH; W is hydroxymethylene or

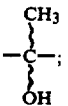

$R_1$ is OH; and $R_4$ is alkyl.

19. A pharmaceutical composition comprising an amount of a compound of claim 1 effective to lower blood pressure in a patient and a pharmaceutically acceptable carrier.

20. A pharmaceutical composition of claim 17 wherein the amount of active ingredient is 0.01 to 100 mg.

21. A method of lowering blood pressure in a patient in need of such treatment comprising administering to the patient an amount of a compound of claim 1 effective to lower blood pressure.

22. A compound of claim 1 wherein A is trans—CH=CH—.

* * * * *